(12) United States Patent
Kim et al.

(10) Patent No.: US 12,220,448 B2
(45) Date of Patent: Feb. 11, 2025

(54) METHOD OF TREATING PATHOGENIC BACTERIAL INFECTIOUS DISEASES

(71) Applicant: KYUNGPOOK NATIONAL UNIVERSITY INDUSTRY-ACADEMIC COOPERATION FOUNDATION, Daegu (KR)

(72) Inventors: Jung Min Kim, Daegu (KR); Jong Sook Jin, Daegu (KR); Shukho Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 983 days.

(21) Appl. No.: 17/262,184

(22) PCT Filed: Aug. 28, 2019

(86) PCT No.: PCT/KR2019/011018
§ 371 (c)(1),
(2) Date: Jul. 11, 2021

(87) PCT Pub. No.: WO2020/055011
PCT Pub. Date: Mar. 19, 2020

(65) Prior Publication Data
US 2022/0175894 A1    Jun. 9, 2022

(30) Foreign Application Priority Data
Sep. 11, 2018  (KR) .................. 10-2018-0108202

(51) Int. Cl.
| | | |
|---|---|---|
| *A61K 38/47* | (2006.01) | |
| *A01N 63/50* | (2020.01) | |
| *A23K 20/147* | (2016.01) | |
| *A23L 33/17* | (2016.01) | |
| *A61P 31/04* | (2006.01) | |
| *C12N 7/00* | (2006.01) | |
| *A01P 1/00* | (2006.01) | |

(52) U.S. Cl.
CPC .............. *A61K 38/47* (2013.01); *A01N 63/50* (2020.01); *A23K 20/147* (2016.05); *A23L 33/17* (2016.08); *A61P 31/04* (2018.01); *C12N 7/00* (2013.01); *C12Y 302/01017* (2013.01); *A01P 1/00* (2021.08); *A23V 2002/00* (2013.01); *C12N 2795/10322* (2013.01); *C12N 2795/10333* (2013.01)

(58) Field of Classification Search
CPC ....... A61K 38/47; A23K 20/147; A23L 33/17; A61P 31/04; A01N 63/50; C12N 7/00; C12N 2795/10322; C12N 2795/10333; C12Y 302/01017; A01P 1/00; A23V 2002/00
See application file for complete search history.

(56) References Cited

U.S. PATENT DOCUMENTS 9,134,312 B2    9/2015  Da Costa Garcia et al.

FOREIGN PATENT DOCUMENTS

| KR | 10-0943041 B1 | | 2/2010 |
|---|---|---|---|
| KR | 10-2011-0130285 | * | 5/2011 |
| KR | 10-2011-0130285 A | | 12/2011 |
| WO | WO02094868 A2 | * | 11/2002 |
| WO | 2004/020635 A1 | | 3/2004 |
| WO | 2010/041970 A2 | | 4/2010 |
| WO | 2010/090542 A2 | | 8/2010 |

OTHER PUBLICATIONS

Maguire et al. Principles of Infectious Diseases: Transmission, Diagnosis, Prevention, and Control, 2017, International Encyclopedia of Public Health, 6: 22-29 (Year: 2017).*
Esdaile, B. Dermatitis, 2017, Top Doctors United Kingdom, https://www.topdoctors.co.uk/medical-dictionary/dermatitis (Year: 2017).*
Baig et al., Infective endocarditis, Clinical Medicine, 2010, 10(2): 188-191 (Year: 2010).*
Barreto et al., Infectious diseases epidemiology, Journal of Epidemiology and Community Health, 60(3): 192-195 (Year: 2006).*
Badawy et al. (Viruses, 2020, vol. 12 (604) pp. 1-20).*
International Search Report for PCT/KR2019/011018 mailed Nov. 29, 2019 from Korean Intellectual Property Office.
Rahman, M. et al., "Characterization of induced Staphylococcus aureus bacteriophage SAP-26 and its anti-biofilm activity with rifampicin", Biofouling. 2011, vol. 27, No. 10, pp. 1087-1093.
NCBI. GenBank Accession No. AOC01812.1. Sequence 575 from patent U.S. Pat. No. 9134312. Aug. 13, 2016.

* cited by examiner

*Primary Examiner* — Hope A Robinson
(74) *Attorney, Agent, or Firm* — Revolution IP, PLLC

(57) ABSTRACT

The invention relates to a method of preventing or treating pathogenic bacterial infectious diseases by providing a pharmaceutical composition comprising a LysSAP26 protein, wherein the LysSAP26 protein is a recombinant protein composed of an amino acid sequence derived from the bacteriophage genome and has the amino acid sequence set forth in SEQ ID NO: 1 as an active ingredient, and administering the pharmaceutical composition to a subject.

2 Claims, 2 Drawing Sheets
Specification includes a Sequence Listing.

[FIG. 1]
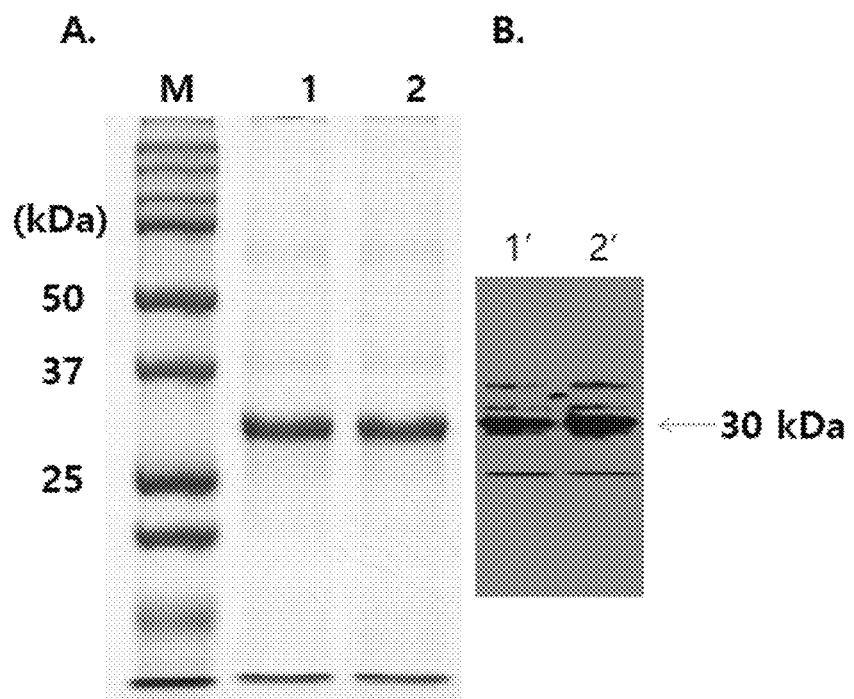

[FIG. 2]
A.
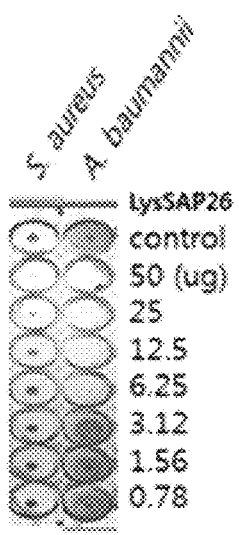
B.
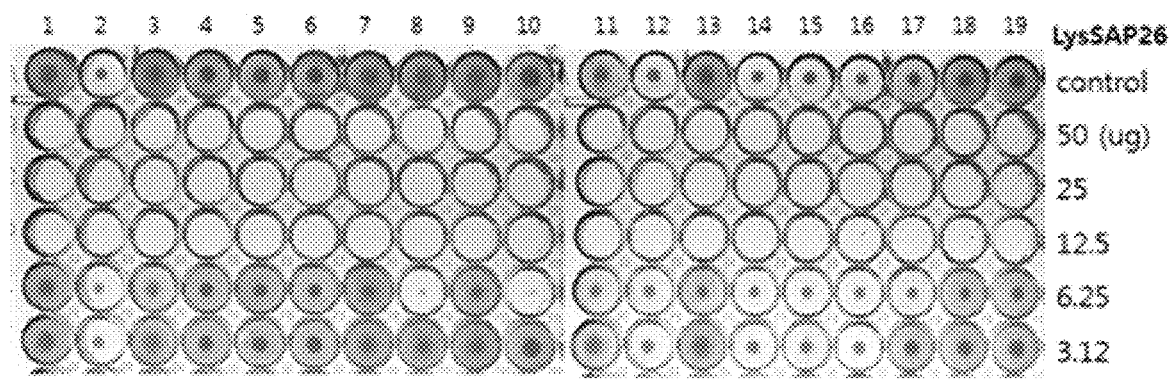
C.
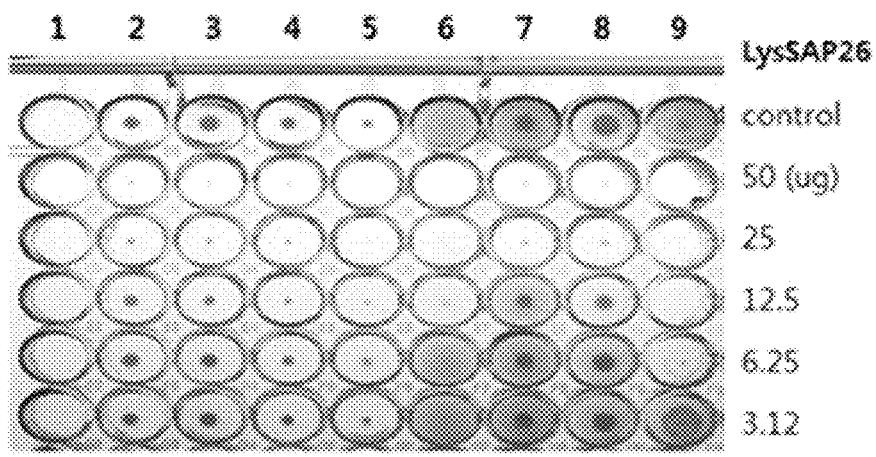

SEQUENCE LISTING

```
<160> NUMBER OF SEQ ID NOS: 4

<210> SEQ ID NO 1
<211> LENGTH: 259
<212> TYPE: PRT
<213> ORGANISM: Siphoviridae bacteriophage SAP26

<400> SEQUENCE: 1

Met Lys Thr Tyr Ser Glu Ala Arg Ala Arg Leu Arg Trp Tyr Gln Gly
1               5                   10                  15

Arg Tyr Ile Asp Phe Asp Gly Trp Tyr Gly Tyr Gln Cys Ala Asp Leu
            20                  25                  30

Ala Val Asp Tyr Ile Tyr Trp Leu Leu Glu Ile Arg Met Trp Gly Asn
        35                  40                  45

Ala Lys Asp Ala Ile Asn Asn Asp Phe Lys Asn Met Ala Thr Val Tyr
    50                  55                  60

Glu Asn Thr Pro Ser Phe Val Pro Gln Ile Gly Asp Val Ala Val Phe
65                  70                  75                  80

Thr Lys Gly Ile Tyr Lys Gln Tyr Gly His Ile Gly Leu Val Phe Asn
                85                  90                  95

Gly Gly Asn Thr Asn Gln Phe Leu Ile Leu Glu Gln Asn Tyr Asp Gly
            100                 105                 110

Asn Ala Asn Thr Pro Ala Lys Leu Arg Trp Asp Asn Tyr Tyr Gly Cys
        115                 120                 125

Thr His Phe Ile Arg Pro Lys Tyr Lys Ser Glu Gly Leu Met Asn Lys
    130                 135                 140

Ile Thr Asn Lys Val Lys Pro Pro Ala Gln Lys Ala Val Gly Lys Ser
145                 150                 155                 160

Ala Ser Lys Ile Thr Val Gly Ser Lys Ala Pro Tyr Asn Leu Lys Trp
                165                 170                 175

Ser Lys Gly Ala Tyr Phe Asn Ala Lys Ile Asp Gly Leu Gly Ala Thr
            180                 185                 190

Ser Ala Thr Arg Tyr Gly Asp Asn Arg Thr Asn Tyr Arg Phe Asp Val
        195                 200                 205

Gly Gln Ala Val Tyr Ala Pro Gly Thr Leu Ile Tyr Val Phe Glu Ile
    210                 215                 220

Ile Asp Gly Trp Cys Arg Ile Tyr Trp Asn Asn His Asn Glu Trp Ile
225                 230                 235                 240

Trp His Glu Arg Leu Ile Val Lys Glu Val Phe Leu Glu His His His
                245                 250                 255

His His His

<210> SEQ ID NO 2
<211> LENGTH: 780
<212> TYPE: DNA
<213> ORGANISM: Siphoviridae bacteriophage SAP26

<400> SEQUENCE: 2
```

-continued

```
atgaaaacat acagtgaagc aagagcaagg ttacgttggt atcaaggtag atatattgat        60
tttgacggtt ggtatggtta ccaatgtgca gatttagcag ttgattacat ttattggttg       120
ttagaaatta gaatgtgggg aaatgcaaaa gatgcaatca ataacgattt taaaaacatg       180
gcaacagtat atgaaaacac accatcgttt gttccacaaa taggtgatgt ggctgtattt       240
accaaaggaa tatataaaca atacggtcat attggtttag tgtttaatgg tggtaataca       300
aaccaatttt taattttgga acagaactat gacggtaacg caaatacgcc tgcaaagtta       360
cgttgggata attattacgg ctgtactcac tttattagac ctaagtataa aagtgagggc       420
ttaatgaata agatcacaaa taaagttaaa ccacctgctc aaaaagcagt cggtaaatct       480
gcaagtaaaa taacagttgg aagtaaagcg ccttataacc ttaaatggtc aaaaggtgct       540
tattttaatg cgaaaatcga cggcttaggt gctacttcag ccactagata cggtgataat       600
cgtactaact atagattcga tgttggacag gctgtatacg cgcctggaac attaatatat       660
gtgtttgaaa ttatagatgg ttggtgtcgc atttattgga acaatcataa tgagtggata       720
tggcatgaga gattgattgt gaaagaagtg tttctcgagc accaccacca ccaccactga       780
```

<210> SEQ ID NO 3
<211> LENGTH: 31
<212> TYPE: DNA
<213> ORGANISM: Artificial Sequence
<220> FEATURE:
<223> OTHER INFORMATION: Primer (nde1-SAPlys)

<400> SEQUENCE: 3
gggaattcca tatgaaaaca tacagtgaag c         31

<210> SEQ ID NO 4
<211> LENGTH: 30
<212> TYPE: DNA
<213> ORGANISM: Artificial Sequence
<220> FEATURE:
<223> OTHER INFORMATION: Primer (xho1-SAPlys)

<400> SEQUENCE: 4
atccgctcga gaaacacttc tttcacaatc          30

METHOD OF TREATING PATHOGENIC BACTERIAL INFECTIOUS DISEASES

CROSS REFERENCE TO PRIOR APPLICATIONS

This application is the 35 U.S.C. 371 national stage of International application PCT/KR2019/011018 filed on Aug. 28, 2019; which claims priority to Korean Patent Application No. 10-2018-0108202 filed on Sep. 11, 2018. The entire contents of each of the above-identified applications are hereby incorporated by reference.

TECHNICAL FIELD

The present invention relates to a use of a recombinant antibacterial enzyme LysSAP26 that effectively kills pathogenic bacteria, and more specifically to a pharmaceutical composition, antibiotics, disinfectants, food additives, or feed additives for killing pathogenic bacteria comprising the antibacterial protein as an active ingredient for preventing or treating infectious diseases caused by pathogenic bacteria dissolved by LysSAP26.

BACKGROUND ART

As the resistance of pathogenic bacteria to multidrug antimicrobial agents increases due to misuse and abuse of antimicrobial agents, the number of cases that are difficult to treat with antibiotics has increased significantly, resulting in a serious health problem, and the development of new antimicrobial agents to cope with this is urgently needed. Bacteriophage, which has a specific killing ability for bacteria, is being studied as a new antimicrobial alternative drug that is attracting attention, and research and development to formulate it using the antibacterial substance possessed by bacteriophage are in progress.

Bacteriophage is a bacterial virus that infects host bacteria according to their biological life history, reproduces a large amount of phage, and generates proteins which penetrate or degrade the bacterial cell wall in the process of being killed by a large amount of phage in the host bacteria's cells and these proteins break down the cell wall composed of peptidoglycans, causing the cell wall to break down, thereby killing the bacteria.

The bacteriophage-derived antibacterial proteins invented so far are limited to gram-positive target bacteria. The reason that the antimicrobial proteins against gram-negative bacteria have insufficient effect is that when the purified antimicrobial proteins are treated outside the bacteria, the outer membrane prevents the antibacterial protein from reaching the peptidoglycan cell wall. For this reason, the use of antimicrobial proteins that degrade cell walls has been biased toward development for gram-positive bacteria, and therefore, if the antimicrobial protein can effectively kill gram-negative bacteria, it can be spotlighted as a very promising antibacterial agent.

The World Health Organization (WHO) designated the carbapenem-resistant *Acinetobacter baumannii* (CRAB) as one of the most dangerous bacteria in the 21st century and reported that the development of a therapeutic agent was urgent. Patients having immunosuppression, chronic lung disease and adult chronic disease are very susceptible to infection by CRAB, and long-term hospitalized patients can be in very critical condition from pneumonia, bloodstream infection, and wound infection. Accordingly, a recombinant protein having an antibacterial action on both gram-positive bacteria and gram-negative bacteria can be widely used as an antibacterial agent to treat multidrug-resistant CRAB bacterial infections.

DISCLOSURE

Technical Problem

An object of the present invention is to provide a pharmaceutical composition for preventing or treating pathogenic bacterial infectious diseases comprising a LysSAP26 protein as an active ingredient.

Another object of the present invention is to provide antibiotics, disinfectants, a food additive and a feed additive for killing pathogenic bacteria comprising a LysSAP26 protein as an active ingredient.

Technical Solution

In order to achieve the above object, the present invention provides a pharmaceutical composition for preventing or treating pathogenic bacterial infectious diseases comprising a LysSAP26 protein, wherein the LysSAP26 protein comprises an amino acid sequence represented by SEQ ID NO: 1 as an active ingredient.

Also, the present invention provides an antibiotic for killing pathogenic bacteria comprising a LysSAP26 protein, wherein the LysSAP26 comprises an amino acid sequence represented by SEQ ID NO: 1 as an active ingredient.

In addition, the present invention provides a disinfectant for killing pathogenic bacteria comprising a LysSAP26 protein, wherein the LysSAP26 comprises an amino acid sequence represented by SEQ ID NO: 1 as an active ingredient.

Furthermore, the present invention provides a food additive for killing pathogenic bacteria comprising a LysSAP26 protein, wherein the LysSAP26 comprises an amino acid sequence represented by SEQ ID NO: 1 as an active ingredient.

In addition, the present invention provides a feed additive for killing pathogenic bacteria comprising a LysSAP26 protein, wherein the LysSAP26 comprises an amino acid sequence represented by SEQ ID NO: 1 as an active ingredient.

Advantageous Effects

The present invention relates to the use of the recombinant antibacterial enzyme LysSAP26 to effectively kill pathogenic bacteria. LysSAP26, a recombinant protein composed of an amino acid sequence derived from the bacteriophage genome of the present invention, exhibits killing ability against pathogenic bacteria including *Acinetobacter baumannii*, and thus can prevent or treat infectious diseases caused by these bacteria, and can be widely used in antibiotics, disinfectants, food additives, feed additives, and the like. In particular, the LysSAP26 uses peptidoglycan, which is a component of the cell wall of bacteria, as a substrate, and exhibits bacterial killing ability due to peptidoglycan degradation. The peptidoglycan exists only in bacteria and not in humans or animals, and thus there is an advantage that LysSAP26 of the present invention is safe because it does not affect humans and animals, and can be applied to the pharmaceutical industry, food industry, biotechnology, etc., as well as can effectively kill bacteria in a target place or a target substance without problems of resistance to multidrug antimicrobial agents.

DESCRIPTION OF DRAWINGS

FIG. 1 shows image of SDS-PAGE analysis after protein purification of LysSAP26, which was confirmed by performing western analysis using a specific antibody that recognizes the six histidine amino acid sequences of LysSAP26. In FIG. 1A, M is a protein size marker, 1 and 2 are samples of two fractions obtained by harvesting LysSAP26 on a Ni-NTA column and FIG. 1B (1' and 2') shows a Western test result using anti-6×His monoclonal antibody against LysSAP26 for samples 1 and 2.

FIG. 2 illustrates (A) showing the results of the bacterial killing ability of LysSAP26 against the clinical isolates of methicillin-resistant *Staphylococcus aureus* (MRSA) ATCC 33691 and *Acinetobacter baumannii*, (B) showing the results of the bacterial killing ability of LysSAP26 against two standard strains of *Acinetobacter baumannii* (ATCC 17978, ATCC 19606), 1656-2, a multi-drug clinical strain, and 16 strains of carbapenem-resistant *Acinetobacter baumannii* (CRAB). 1: *A. baumannii* 1656-2, 2: *A. baumannii* ATCC 17978, 3: *A. baumannii* ATCC 19606, 4-6: *A. baumannii* ST357 strains, 7-9: *A. baumannii* ST208 strains, 10: *A. baumannii* ST552 strain, 11-13: *A. baumannii* ST191 strains, 14-16: *A. baumannii* ST369 strains, 17-19: *A. baumannii* ST229 strains, (C) showing the results of a bacterial killing ability test for various bacteria. 1 to 9 are *Streptococcus agalactiae* ATCC 13813, *Staphylococcus aureus* ATCC 33591, *Staphylococcus aureus* ATCC 25923, *Staphylococcus epidermidis* 1 strain, *Corynebacterium diphtheria* 1 strain, *Bacillus cereus* ATCC 14579, *Salmonella typhimurium* ATCC 14028, *Escherichia coli* ATCC 25922 and *Acinetobacter baumannii* 1 strain in order.

BEST MODE

The inventors of the present invention transformed DNA encoding a recombinant protein (referred to as 'LysSAP26') derived from bacteriophage SAP26 into *E. coli* together with a vector to express the protein, and confirmed that the protein exhibited killing activity in *Staphylococcus aureus* and in particular, it can be used as an alternative antimicrobial agent against *Acinetobacter baumannii* bacteria and completed the present invention. On the other hand, SAP26 bacteriophage, the source of LysSAP26, can kill *Staphylococcus aureus* but cannot kill *Acinetobacter baumannii* whereas LysSAP26 exhibits an effective bacterial killing ability showing an antibacterial effect on the bacteria.

The present invention provides a pharmaceutical composition for preventing or treating pathogenic bacterial infectious diseases comprising a LysSAP26 protein, wherein the LysSAP26 protein comprises an amino acid sequence represented by SEQ ID NO: 1 as an active ingredient.

Specifically, the LysSAP26 protein may be derived from a bacteriophage SAP26 (KCTC 11665BP) of Siphoviridae, but it is not limited thereto. The present inventors induced and isolated a novel bacteriophage from a clinical isolate of *Staphylococcus aureus* and deposited the isolated bacteria to the Korea Human Gene Bank (KHGB) of the Korea Research Institute of Bioscience & Biotechnology (KRIBB) on Mar. 11, 2010 (accession number KCTC 11665BP). The address of the KRIBB is 125 Gwahak-ro, Yuseong-gu, Daejeon 334141, Republic of Korea. The deposit was made under Budapest Treaty, and that all restrictions imposed by the depository will be irrevocably removed upon the granting of the patent.

Specifically, the gene encoding the LysSAP26 protein may comprise a nucleotide sequence represented by SEQ ID NO: 2, but it is not limited thereto.

In detail, the pathogenic bacteria may be the pathogenic bacteria are any one selected from the group consisting of *Acinetobacter baumannii*, *Staphylococcus aureus*, *Staphylococcus epidermidis*, *Salmonella typhimurium*, *Escherichia coli*, *Corynebacterium diphtheria*, *Bacillus cereus* and *Streptococcus agalactiae*, but it is not limited thereto.

Specifically, the pathogenic bacterial infectious disease may be sepsis, pneumonia, food poisoning, infection, impetigo, purulent disease, acute dermatitis, wound infection, bacteremia, endocarditis or enteritis, but it is not limited thereto.

The LysSAP26 protein of the present invention uses peptidoglycan, which is a component of the cell wall of bacteria, as a substrate to degrade and disrupt the cell wall, thereby killing the bacteria. The peptidoglycan exists only in bacteria and not in humans or animals, and thus there is an advantage that the protein of the present invention is safe because it does not affect humans and animals, and can be applied to the pharmaceutical industry, food industry, biotechnology, etc., as well as can effectively kill bacteria in a target place or a target substance without problems of resistance to multi-drug antimicrobial agents.

As used herein, the term 'treatment' refers to the prevention, inhibition and alleviation of infectious diseases caused by pathogenic bacteria.

When the composition of the present invention is a pharmaceutical composition, for administration, it may include a pharmaceutically acceptable carrier, excipient or diluent in addition to the above-described active ingredients. Examples of the carrier, excipient and diluent include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils.

The pharmaceutical compositions of the present invention can be formulated and used in the form of oral formulations such as powders, granules, tablets, capsules, suspensions, emulsions, syrups, aerosols, external preparations, suppositories, or sterile injectable solutions according to a conventional method. In detail, when formulated, it may be prepared using diluents or excipients such as fillers, weighting agents, binders, wetting agents, disintegrants and surfactants that are commonly used. Solid preparations for oral administration include tablets, pills, powders, granules, capsules, and the like, but they are not limited thereto. Such a solid preparation may be prepared by mixing at least one excipient, for example, starch, calcium carbonate, sucrose, lactose, gelatin, etc. in addition to the active ingredient. Further, in addition to simple excipients, lubricants such as magnesium stearate and talc may also be used. It can be prepared by adding various excipients such as wetting agents, sweetening agents, fragrances, preservatives, and the like, in addition to liquids and liquid paraffins for oral use. Formulations for parenteral administration include sterile aqueous solutions, non-aqueous solvents, suspensions, emulsions, lyophilized formulations, and suppositories. As the non-aqueous solvent and suspending agent, propylene glycol, polyethylene glycol, vegetable oil such as olive oil, injectable ester such as ethyl oleate, and the like may be used. As a base for suppositories, witepsol, macrosol, Tween 61, cacao butter, laurin, glycerogelatin, and the like may be used.

A suitable dosage of the pharmaceutical composition of the present invention varies depending on the condition and weight of the patient, the severity of the disease, the form of the drug, and the time, but can be appropriately selected by a person skilled in the art. Thus, the daily dosage of the pharmaceutically acceptable salt is preferably 0.001 mg/kg to 50 mg/kg, and may be administered once to several times a day as necessary.

In addition, the present invention provides an antibiotic for killing pathogenic bacteria comprising a LysSAP26 protein, wherein the LysSAP26 comprises an amino acid sequence represented by SEQ ID NO: 1 as an active ingredient. As used herein, the term "antibiotics" refers to cosmetic or pharmaceutical preservatives, fungicides and antibacterial agents.

Cosmetics contain oil or water as their main components, and because there are many combinations of glycerin or sorbitol as carbon sources of microorganisms, amino acid derivatives and proteins as nitrogen sources, it is easy for microorganisms such as bacteria. In addition, it can be said that the risk of contamination by microorganisms is much greater because the period of use is very long compared to that of food. It is essential to add an antibacterial agent to protect cosmetics for a long time from discoloration or deodorant caused by microbial contamination due to use.

The LysSAP26 protein of the present invention has excellent ability to kill a wide range of bacteria compared to conventional antimicrobial agents. If the protein is used as an antimicrobial agent, unlike conventional antimicrobial agents, it has the advantage of not inducing tolerance or resistance of bacteria to provide an antibiotic material having a longer life cycle compared to the conventional antibiotic material. While most of the antibiotics face increased resistance, the range of use decreases, whereas the antimicrobial agent comprising the protein of the present invention as an active ingredient can fundamentally solve the problem of resistance to antibacterial agents, thereby increasing the product lifespan as an antimicrobial agent.

Therefore, an antibiotic comprising the protein of the present invention having killing activity to pathogenic bacteria as an active ingredient can be usefully used as an antibiotic having excellent antibacterial, bactericidal and antiseptic effects.

In addition, the present invention provides a disinfectant for killing pathogenic bacteria comprising a LysSAP26 protein, wherein the LysSAP26 comprises an amino acid sequence represented by SEQ ID NO: 1 as an active ingredient.

The disinfectant comprising the LysSAP26 protein of the present invention having the ability to selectively kill pathogenic bacteria as an active ingredient can be usefully used as a disinfectant for hospitals and health care to prevent hospital infection, and also as a disinfectant for general life, food and cooking places and facilities, livestock housing in the livestock industry.

In addition, the present invention provides a food additive for killing pathogenic bacteria comprising a LysSAP26 protein, wherein the LysSAP26 comprises an amino acid sequence represented by SEQ ID NO: 1 as an active ingredient.

Food additives of the present invention may contain preservatives, fungicides, antioxidants, spices, seasonings, sweeteners, flavoring agents, expanding agents, reinforcing agents, improving agents, emulsifying agents, various nutrients, synthetic flavoring agents such as synthetic flavoring agents and natural flavoring agents, colorants, coloring agents, fillers (cheese, chocolate etc.), pectic acid and its salts, alginic acid and its salts, organic acids, protective colloid thickeners, pH adjusting agents, stabilizers, antifoaming agents, solvents, release agents, preservatives, quality improving agents, glycerin, alcohols, carbonating agents used in carbonated drinks, and the like, which are additionally added to food, and can be added by dipping in, spraying to or mixing with food.

In addition, the present invention provides a feed additive for killing pathogenic bacteria comprising a LysSAP26 protein, wherein the LysSAP26 comprises an amino acid sequence represented by SEQ ID NO: 1 as an active ingredient.

The LysSAP26 protein of the present invention can be used as an additive for livestock feed and drinking water for livestock for the purpose of preventing or treating bacterial infections and can improve or maintain animal feed intake, growth, feed efficiency, survival rate, feeding condition, production capacity, etc.

Hereinafter, the present invention will be described in more detail through examples. These examples are only intended to illustrate the present invention in more detail, and it will be apparent to those skilled in the art that the scope of the present invention is not limited by these examples according to the gist of the present invention.

<Example 1> Preparation and Purification of Recombinant Protein LysSAP26 Composed of Amino Acid Sequence Derived from Bacteriophage Genome To obtain a fragment containing the open reading frame 26 (ORF26) of the bacteriophage SAP26 (Accession No. KCTC 11665BP) of Siphoviridae having specific killing ability for *Staphylococcus aureus*, gDNA of the bacteriophage SAP26 was extracted. A polymerase chain reaction (PCR) was performed using the gDNA as a template, and the primers used were as follows: nde1-SAPlys: GGGAATTC-CATATGAAAACATACAGTGAAGC (SEQ ID NO: 3), xho1-SAPlys: ATCCGCTCGAGAAACACTTCTTT-CACAATC (SEQ ID NO: 4). The PCR fragment was obtained by eluting a band of a desired size after electrophoresis on an agarose gel.

The PCR fragment was digested by treating with restriction enzymes NdeI and XhoI, and then ligated with an expression vector (pET21a) digested with the same enzyme. When *E. coli* BL21 (DE3) was transformed with the prepared vector (LysSAP26-pET21a) and then cultured in LB liquid medium to which 100 μg/ml of ampicillin was added, until the absorbance of the bacteria became 0.6 (600 nm wavelength). Next, IPTG (isopropyl β-D-1-thiogalactopyranoside) was added so that the final concentration was 0.1 mM, and incubated at 18° C. for 16 hours to induce protein expression.

Thereafter, after harvesting the bacteria, the bacteria were disrupted with a lysis buffer [50 mM Tris-HCl (pH 8.0), 200 mM NaCl] and an ultrasonic sonicator. The crushed bacterial lysate was centrifuged to take a supernatant, and injected into a Ni-NTA column, LysSAP26 proteins tagged with six histidines at the C-terminus were purified using elution buffer [500 mM imidazole, 50 mM Tris-Cl (pH 8.0), 200 mM NaCl].

To confirm the purified LysSAP26 protein, after performing SDS-PAGE (12%) and Coomassie blue staining, LysSAP26 protein was confirmed at 30.1 kDa as shown in FIG. 1 and Western analysis using an anti-6×His monoclonal antibody confirmed that the 30.1 kDa protein was 6×His tagged LysSAP26.

In FIG. 1A, M is a protein size marker, 1 and 2 are samples of two fractions obtained by harvesting LysSAP26 on a Ni-NTA column and FIG. 1B (1' and 2') shows a Western test result using anti-6×His monoclonal antibody against LysSAP26 for samples 1 and 2.

The amino acid sequence and number of LysSAP26 is composed of 259 amino acids including histidine tag represented by SEQ ID NO: 1 and has a total size of 30.1 kDa. The gene coding sequence is 777 bp represented by SEQ ID NO: 2.

<Example 2> Analysis of Ability of LysSAP26 to Kill Bacteria

The bacterial killing ability of LysSAP26 was performed for gram-positive bacterium *Staphylococcus aureus* ATCC 33591 and gram-negative bacterium *Acinetobacter baumannii* 2 standard strains (ATCC 17978, ATCC 19606) and 16 clinical strains of multidrug-resistant *Acinetobacter baumannii* 1656-2, carbapenem-resistant *Acinetobacter baumannii* (CRAB) as follows (FIG. 2). CRAB strains of 16 were selected according to the sequence type (ST) subspecies of *Acinetobacter baumannii*: ST357 3 strains, ST208 3 strains, ST552 1 strain, ST191 3 strains, ST369 3 strains, and ST229 3 strains. The killing ability of various other bacteria was also analyzed, and the target bacteria are as follows: *Streptococcus agalactiae* ATCC 13813, *Staphylococcus aureus* ATCC 25923, *Staphylococcus epidermidis* 1 strain, *Corynebacterium diphtheria* 1 strain, *Bacillus cereus* 1 strain, *Salmonella typhimurium* ATCC 14028, *Escherichia coli* ATCC 25922.

Each bacteria was prepared to have a number of bacteria of $5\times10^4$ CFU/well using Luria Bertani (LB) broth, and The purified LysSAP26 protein was added so as to be 3.12, 6.25, 12.5, 25 and 50 ug/well, respectively, and reacted at 35° C. for 16 hours, and then the degree of growth (turbidity) of bacteria was observed.

As a result, the growth of bacteria was observed in all the control groups (−LysSAP26) in the well plate, whereas in the test group (+LysSAP26), *Staphylococcus aureus* showed no growth of bacteria at an enzyme amount of 50 μg or more (FIG. 2A), and *Acinetobacter baumannii* bacteria showed a transparent liquid phase in which no bacterial growth was observed in the reaction solution treated up to 12.5 ug, thereby confirming that It had a killing effect (FIG. 2B). In addition, as a result of the bacterial killing ability test for various bacteria, in 50 μg of LysSAP26 treatment, *Staphylococcus aureus* ATCC 33591, *Staphylococcus aureus* ATCC 25923, *Staphylococcus epidermidis* 1 strain (FIG. 2, C, Nos. 2-4), *Salmonella typhimurium* ATCC 14028, and *Escherichia coli* ATCC 25922 (FIG. 2, C, Nos. 7 and 8) were killed, and in 25 μg of LysSAP26 treatment, *Corynebacterium diphtheria* 1 strain and *Bacillus cereus* ATCC 14579 (FIG. 2, C, Nos. 5 and 6), *Streptococcus agalactiae* 1 strain and *Acinetobacter baumannii* 1 strain were killed to 6.25 ug of LysSAP26 enzyme-treated concentration (FIG. 2, C, Nos. 1 and No. 9).

Meanwhile, examples of preparations using the protein of the present invention are exemplified below, but this is not intended to limit the present invention, but is intended to be described in detail.

Formulation Example 1: Preparation of Powder

Recombinant protein LysSAP26 300 mg
Lactose 100 mg
Talc 10 mg

The above ingredients are mixed and filled in an airtight cloth to prepare a powder.

Formulation Example 2: Preparation of Tablets

Recombinant protein LysSAP26 300 mg
Corn starch 100 mg
Lactose 100 mg
Magnesium stearate 2 mg After mixing the above ingredients, tablets are prepared by compressing according to a conventional tablet preparation method.

Formulation Example 3: Preparation of Capsules

Recombinant protein LysSAP26 300 mg
Crystalline cellulose 3 mg
Lactose 14.8 mg
Magnesium stearate 0.2 mg According to a conventional capsule preparation method, the above ingredients are mixed and filled into gelatin capsules to prepare a capsule.

Formulation Example 4: Preparation of Injection Formulation

Recombinant protein LysSAP26 300 mg
Mannitol 180 mg
Sterile distilled water for injection 2974 mg
$Na_2HPO_4 \cdot 2H_2O$ 26 mg According to a conventional injection preparation method, it is prepared with the above ingredients per ampoule (2).

Formulation Example 5: Preparation of Liquid Formulation

Recombinant protein LysSAP26 300 mg
Isomerized sugar 10 g
Mannitol 5 g
Purified water appropriate amount According to a conventional preparation method of liquid formulation, each ingredient is added to purified water to dissolve it, lemon zest is added and the above ingredients are mixed, purified water is added to adjust the total amount to 100, then filled in a brown bottle for sterilization to prepare liquid formulation.

Formulation Example 6: Preparation of Food Additives

A milk composition according to the present invention was prepared by adding 1% (w/v) of the recombinant protein LysSAP26 of the present invention to 200 ml of commercially available S-manufactured milk.

Formulation Example 7: Preparation of Feed Additive

A feed additive was prepared according to the method for producing a feed additive by mixing 100 g of the recombinant protein LysSAP26 of the present invention and an appropriate amount of an excipient.

Formulation Example 8: Feed Preparation

A feed was prepared according to a conventional feed preparation method by mixing recombinant protein of the present invention LysSAP26 of 50 g, mushroom medium of 200 g, wheat bran of 30 g, beet pulp of 50 g, rice DDGS (Distillers Dried Grains with Solubles) of 220 g, corn flakes of 200 g, whole soybean of 40 g, starch pulp of 100 g, corn silage of 200 g, corn cob of 180 g, bean-curd dregs of 400 g, ryegrass of 323 g, geolite of 14 g and tapioca of 40 g.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is indicated by the claims to be described later, and all changes or modified forms derived from the meaning and scope of the claims and their equivalent concepts should be interpreted as being included in the scope of the present invention.

The invention claimed is:

1. A method of treating a pathogenic bacterial infectious disease, comprising:
   administering to a subject a pharmaceutical composition comprising a LysSAP26 protein,
   wherein the LysSAP26 protein has the amino acid sequence set forth in SEQ ID NO: 1 and a pharmaceutically acceptable carrier,
   wherein the pathogenic bacterial infectious disease is caused by carbapenem-resistant *Acinetobacter baumannii* (CRAB), and is selected from the group consisting of sepsis, impetigo, purulent disease, and wound infection, and
   wherein the LysSAP26 protein is obtained from a bacteriophage SAP26 of Siphoviridae deposited as Accession Number KCTC 11665BP.

2. The method of claim 1, wherein a gene encoding the LysSAP26 protein comprises the nucleotide sequence set forth in SEQ ID NO: 2.

* * * * *